United States Patent [19]

Dotzlaf et al.

[11] Patent Number: 5,508,177
[45] Date of Patent: Apr. 16, 1996

[54] PROCESS FOR PURIFICATION OF WATER SOLUBLE PENICILLIN BINDING PROTEIN 2A

[75] Inventors: Joe E. Dotzlaf, Greenwood; Sandhya K. Ghag, Carmel; Wu-Kuang Yeh, Greenwood, all of Ind.

[73] Assignee: Eli Lilly and Company, Indianapolis, Ind.

[21] Appl. No.: 61,894

[22] Filed: May 14, 1993

[51] Int. Cl.$^6$ .......................... C12P 21/04; C12P 21/06; C12N 15/00
[52] U.S. Cl. ................. 435/70.1; 435/69.1; 435/240.2; 435/320.1; 435/252.3; 530/350; 530/412; 530/413; 530/416; 530/417; 530/396
[58] Field of Search ................. 435/70.1, 69.1, 435/240.2, 320.1, 252.3; 530/350, 412, 413, 416, 417, 396

[56] References Cited

PUBLICATIONS

Schultz et al. (1991) Protein Expression & Purification, vol. 2 (5–6): pp. 339–349.
Leidenix et al. (1989) J of Bacteriol. vol 171, No. 10: pp. 5680–5686.
Sofer et al. (Nov./Dec. 1983) Bio Techniques, pp. 198–203.
Mottl, H. et al., 1992, Protein Exp. and Purif. 3:403–409.
Mottl, H. et al., 1991, Eur. J. Biochem. 200:767–773.
Matsuhashi, M. et al., 1986, J. of Bacter. 167(3): 975–980.
Wu, C. Y. et al., 1992, Antimicrob. Agents and Chemoth. 36(3):533–539.
Pierre, J. et al., 1990, Antimicrob. Agents and Chemoth. 34(9):1691–1694.
Murakami, K. et al., 1987, Antimicrob. Agents and Chemoth. 31(9):1307–1311.
Tesch, W. et al., 1988, Antimicrob. Agents and Chemoth. 32(10):1494–1499.
Hartman, B. et al., 1984, J. of Bacter. 158(2):513–516.
Tonin, E. et al., 1986, Antimicrob. Agents and Chemoth. 30(4):577–583.
Ubukata, K. et al., 1985, Antimicrob. Agents and Chemoth. 27(5):851–857.
Adachi, H. et al., 1987, FEBS Letters 226(1):150–154.
Preston, D. A. et al., 1990, Antimicrob. Agents and Chemoth. 34(5):718–721.

*Primary Examiner*—Stephen G. Walsh
*Assistant Examiner*—Elizabeth C. Kemmerer
*Attorney, Agent, or Firm*—Thomas G. Plant

[57] ABSTRACT

The present invention provides processes for isolating in substantially purified form water-soluble penicillin binding protein 2a of *Staphylococcus aureus*.

6 Claims, 6 Drawing Sheets

```
                      Crude Extract
                            │
                            ▼
   Unbound ┌────── Q-Sepharose ──────┐ Bound
           │                          │
           ▼                          ▼
     CM-Sepharose              CM-Sepharose
           │                          │
           ▼                          ▼
     Blue-4 Agarose            Blue-4 Agarose Sephacryl S-200            Sephacryl S-200

Unbound      >99% PBP 2a$^s$      Bound
```

PROCESS FOR PURIFICATION OF WATER SOLUBLE PENICILLIN BINDING PROTEIN 2A

BACKGROUND OF THE INVENTION

This invention relates to protein purification technology. In particular, the invention relates to a process for the purification of water-soluble forms of penicillin binding protein 2a (PBP 2a) of *Staphylococcus aureus*.

*Staphylococcus aureus* resistance to methicillin, a semi-synthetic penicillin, was first reported in 1961 (Barber, 1961, *J. Clin. Pathol.* 14:383–393), shortly after the antibiotic was introduced. Occurrences of methicillin-resistant *S. aureus* (MRSA) infections were rare until the 1980's. However, since that time the incidence of nosocomial infections by MRSA and other methicillin-resistant staphylococci species has been increasing and is now considered a world-wide health concern (Neu, 1992, *Science* 257:1064–1073.

Resistance to methicillin has been attributed to PBP 2a, a product of the *Staphylococcus aureus* mecA gene, which was first characterized by Matsuhashi et al., 1986, *J. Bacteriol.* 196:3508–3514. PBP 2a, a membrane bound protein, putatively functions as a transpeptidase for cell-wall biosynthesis in the presence of β-lactam antibiotics. Wu et al., 1992, *Antimicrobiol. Agents Chemother.* 36:533–539, described the construction of plasmid pEWSA30 which expressed a PBP 2a variant from *Staphylococcus aureus* strain 27r in *Escherichia coli*. This PBP 2a variant is devoid of the region encoding the putative transmembrane domain. Thus, *E. coli* DH5α cells transformed with pEWSA30 produced PBP 2a as a soluble protein when grown on a solid medium.

There have been reports of the purification of other PBPs. A soluble variant of penicillin binding protein 2x (PBP 2x) from *Streptococcus pneumoniae* expressed in *Escherichia coli* was described by Laible et al., 1992, *Eur. J. Biochem.* 207:943–949. Laible et al. purified small amounts of the variant *S. pneumoniae* PBP 2x by dye-ligand chromatography followed by an anion exchange on Mono Q. Mottl and Keck (*Protein Expr. Purif.* 3:403–409 (1992)) described the use of dye-ligand chromatography in protein purification, in particular PBP 4 of *E. coli*.

Compounds having high affinity for PBP 2a would have substantial therapeutic value as antibiotics against MRSA. The structure/function based design of antibiotic compounds useful against staphylococcal infections is dependent upon the ability to characterize the binding domains of penicillin binding proteins produced by methicillin resistant strains of staphylococci. The characteristics of such potential antibiotic binding sites can be determined by x-ray crystallography, nuclear magnetic resonance (NMR), fluorescence spectroscopy, circular dichroism spectroscopy, and electrospray mass spectrometry. A major obstacle in performing these studies on the penicillin binding proteins, particularly PBP 2a, has been the characteristic membrane-bound nature of these proteins. To aid in the characterization of PBP 2a, this invention provides a process for purifying water-soluble forms of PBP 2a (PBP $2a^s$).

DEFINITIONS

Figure 1:
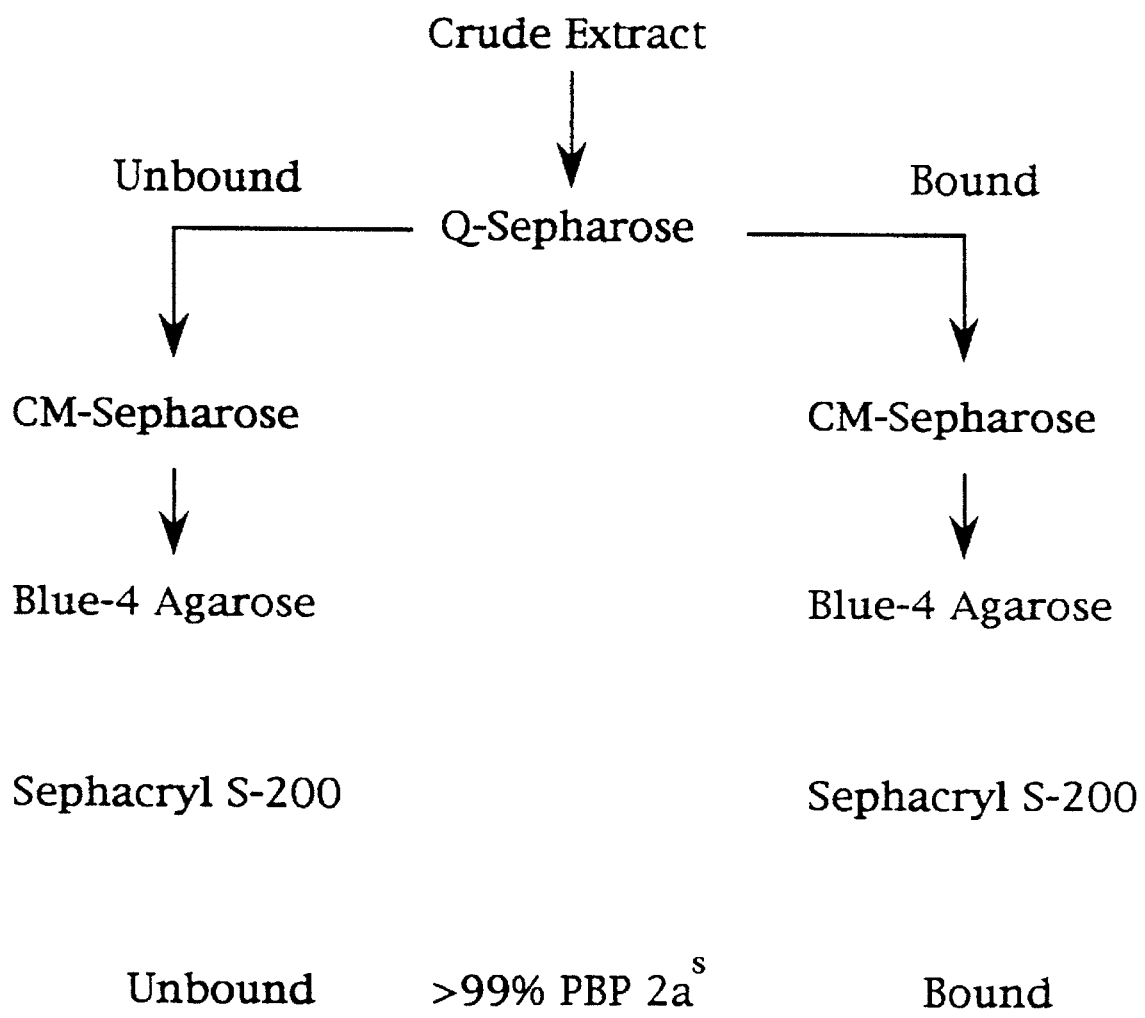
FIG. 1 is a flow chart of the purification process for PBP $2a^s$.
Figure 2:
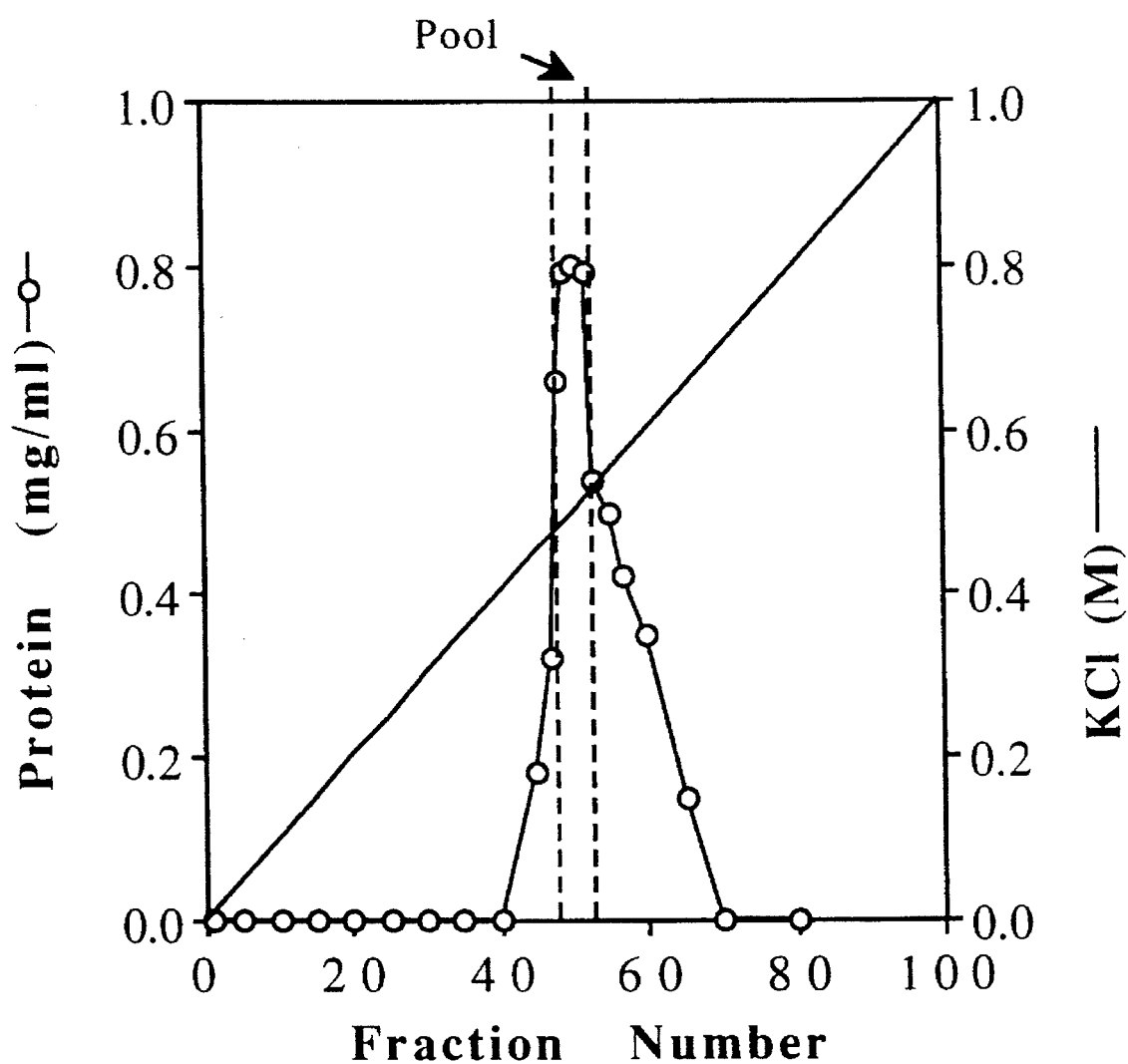
FIG. 2 is the chromatographic purification of "unbound" PBP $2a^s$ following Blue-4 Agarose chromatography.
Figure 3:
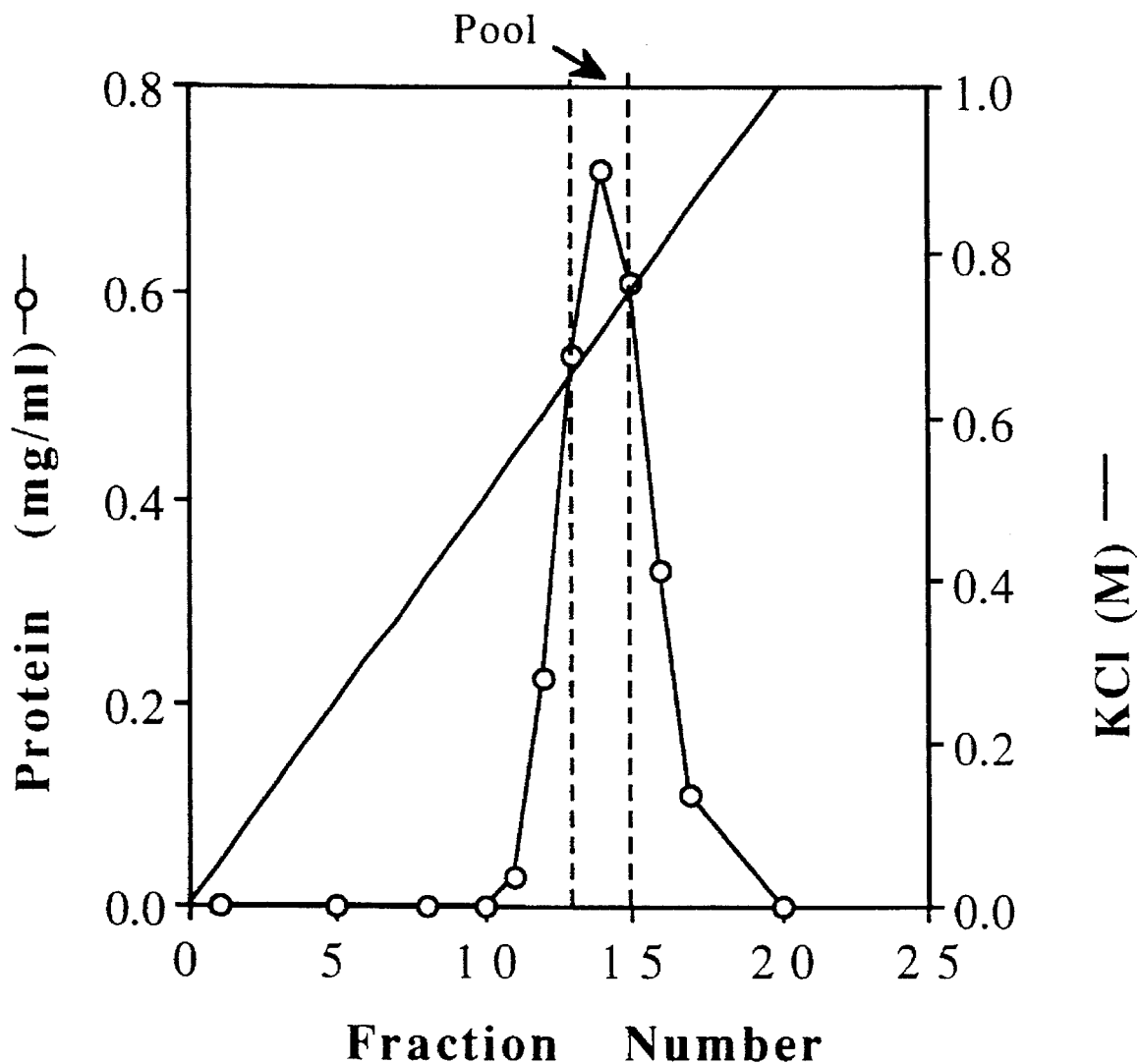
FIG. 3 is the chromatographic purification of "bound" PBP $2a^s$ following Blue-4 Agarose chromatography.
Figure 4:
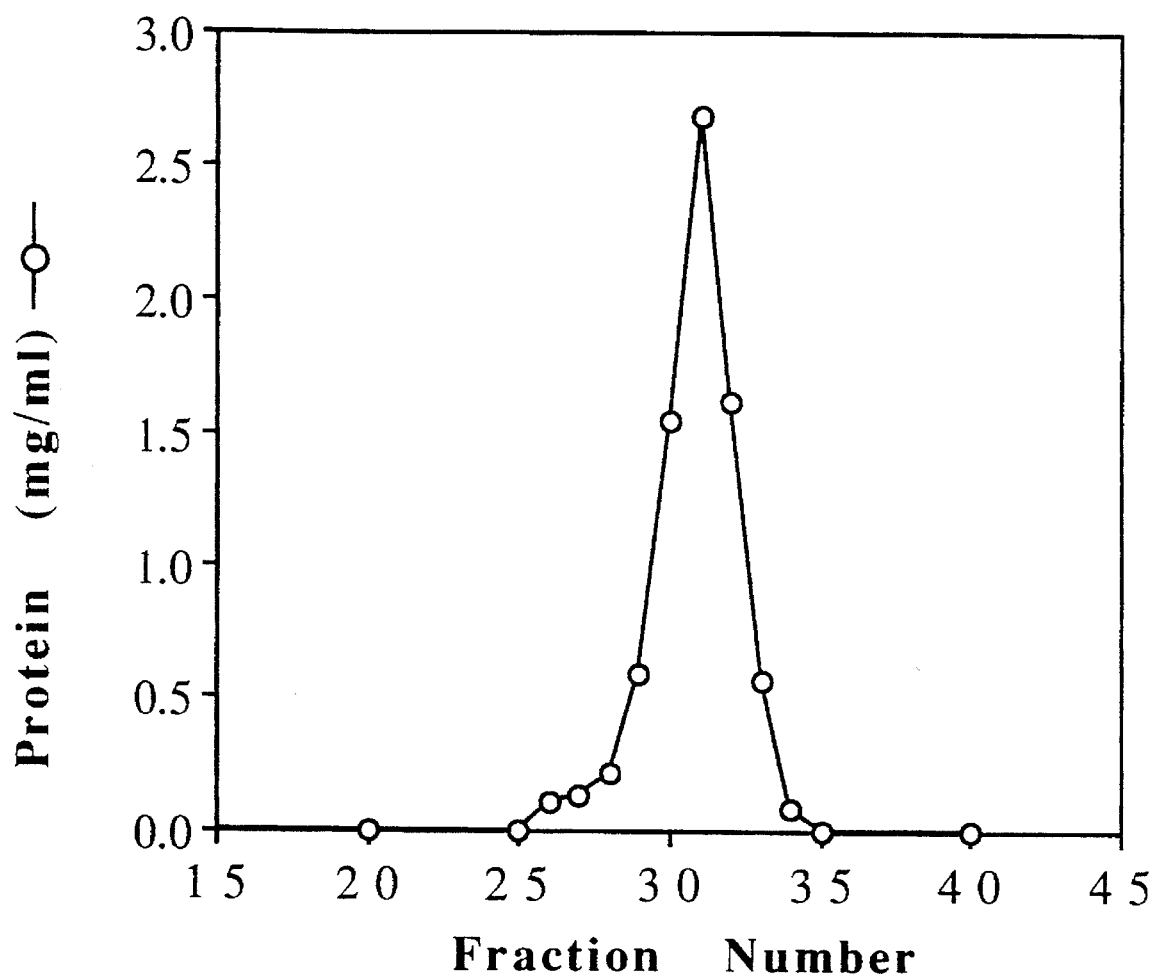
FIG. 4 is the chromatographic purification of unbound PBP $2a^s$ following Sephacryl S-200 chromatography.
Figure 5:
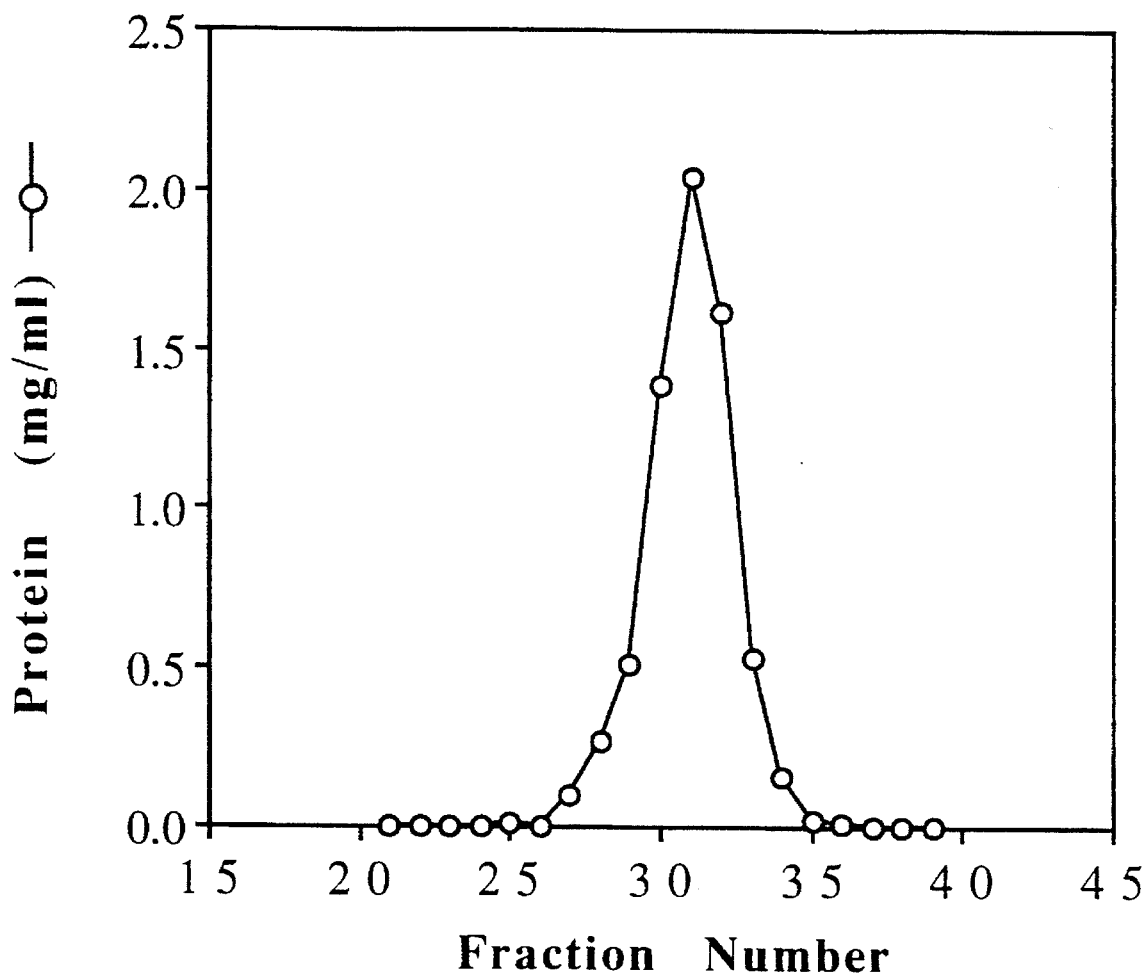
FIG. 5 is the chromatographic purification of bound PBP $2a^s$ following Sephacryl S-200 chromatography.
Figure 6:
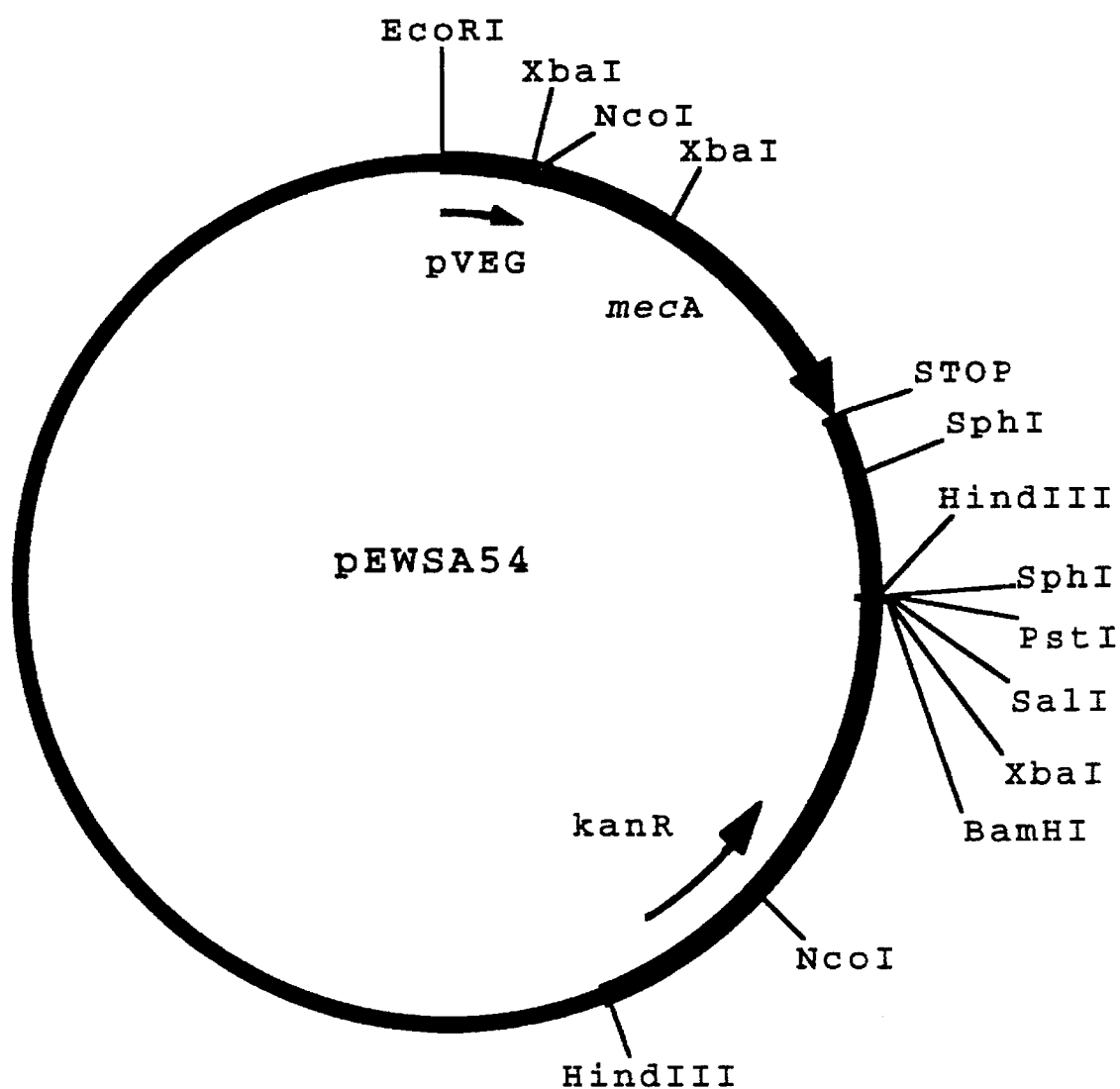
FIG. 6 is a restriction enzyme site and function map of plasmid pEWSA54. This restriction enzyme site and function map is an approximate representation of plasmid pEWSA54. The restriction site information is not exhaustive, there may be more restriction enzyme sites of a given type than are actually shown on the map.

Bound PBP $2a^s$—defines PBP $2a^s$ that binds to an anionic exchange resin.

kanR—DNA encoding the kanamycin resistance genotype.

mecA—Staphylococcus aureus gene encoding penicillin binding protein 2a.

MRSA—methicillin resistant *Staphylococcus aureus*.

MRS—methicillin resistant staphylococci.

PBP 2a—penicillin binding protein 2a from *Staphylococcus aureus*.

PBP $2a^s$—penicillin binding protein 2a that lacks the transmembrane region and is water-soluble.

PBP $2a^s$ 27r—penicillin binding protein 2a derived from *Staphylococcus aureus* 27r. PBP $2a^s$ 27r lacks the transmembrane region and is water-soluble.

PBPs—penicillin binding proteins.

Promoter—a DNA sequence that directs or initiates the transcription of DNA.

pVEG—the vegetative promoter of Bacillus.

Recombinant DNA Expression Vector—any recombinant DNA cloning vector in which a promoter has been incorporated to drive expression of a foreign gene.

Replicon—A DNA sequence that controls and allows for autonomous replication of a plasmid or other vector.

SDS-PAGE—sodium dodecyl sulfate polyacrylamide gel electrophoresis.

Tris—an abbreviation for tris(hydroxymethyl)aminomethane.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Vectors include Recombinant DNA expression vectors.

Unbound PBP $2a^s$—defines PBP $2a^s$ that does not bind to an anionic exchange resin.

SUMMARY OF THE INVENTION

The present invention provides a process for isolating in substantially purified form PBP $2a^s$ from a biological cell comprising:

a) lysing said cell;

b) fractionating the cell lysate to obtain a proteinaceous solution substantially free from cellular debris;

c) contacting the proteinaceous solution obtained in b) with an anion-exchange resin that is not capable of binding the PBP 2a$^s$ contained in the proteinaceous solution;

d) collecting PBP 2a$^s$-containing fractions of the solution that do not bind to the anion-exchange resin;

e) contacting the PBP 2a$^s$-containing fractions of d) with a cation-exchange resin capable of binding the PBP 2a$^s$;

f) eluting the PBP 2a$^s$ from the cation-exchange resin with a linear salt gradient;

g) concentrating and diluting the eluate of step f) to reduce salt concentration;

h) contacting the eluate obtained in g) with a dye-ligand resin capable of binding the PBP 2a$^s$; and i) eluting the PBP 2a$^s$ from the dye-ligand resin with a linear salt gradient.

The present invention also provides a process for isolating in substantially purified form PBP 2a$^s$ from a biological cell comprising:

a) lysing said cell;

b) fractionating the cell lysate to obtain a proteinaceous solution substantially free from cellular debris;

c) contacting the proteinaceous solution obtained in b) with an anion-exchange resin that is capable of binding the PBP 2a$^s$ contained in the proteinaceous solution;

d) eluting the PBP 2a$^s$ from the anion-exchange resin with a linear salt gradient;

e) contacting the PBP 2a$^s$-containing solution obtained in d) with a cation-exchange resin capable of binding the PBP 2a$^s$;

f) eluting the PBP 2a$^s$ from the cation-exchange resin with a linear salt gradient;

g) concentrating and diluting the eluate of step f) to reduce salt concentration;

h) contacting the eluate obtained in g) with a dye-ligand resin capable of binding the PBP 2a$^s$; and i) eluting the PBP 2a$^s$ from the dye-ligand resin with a linear salt gradient.

DETAILED DESCRIPTION OF THE INVENTION

The process of this invention allows the facile preparation of PBP 2a$^s$ that is suitable for x-ray crystallography, nuclear magnetic resonance (NMR), fluorescence spectroscopy, circular dichroism spectroscopy, and electrospray mass spectrometry. Information gained from these studies will provide insight into the structure of the penicillin binding proteins derived from methicillin resistant staphylococci which have a reduced affinity for the binding of penicillin. This information will assist in providing an overall structural picture of the penicillin binding domains of PBP 2a molecules derived from MRS strains. Such a model will provide information useful in the structure/function based design of antibiotic compounds suitable against a broad spectrum of methicillin resistant staphylococci.

Using techniques of recombinant DNA technology, DNA molecules encoding soluble forms of PBPs have been produced. One method of producing these soluble forms is by deleting the DNA encoding the transmembrane region of the PBP 2a molecule. These modified DNA molecules encode a PBP 2a that is not membrane bound when expressed in an appropriate host cell. The method of using recombinant DNA techniques to produce a soluble PBP is described by Wu et al., supra.

The method of this invention applies to water-soluble forms of PBP 2a. Such PBP 2a$^s$ molecules can be expressed in a wide variety of host cells by employing the techniques of recombinant DNA technology. The choice of a particular host cell for the expression of the DNA encoding PBP 2a$^s$ depends to some extent on the particular recombinant DNA expression vector used to drive expression of the PBP 2a$^s$-encoding DNA. Expression in prokaryotic and eukaryotic cells is described by Maniatis et al. (1989), and Kaufmann, *Genetic Engineering Principles and Methods*, ed. J. K. Setlow, Plenum Press 9:155, (1988). Recombinant DNA compounds and expression vectors encoding PBP 2a are disclosed and claimed in U.S. patent application Ser. No. 07/672,704 which was filed on Mar. 19, 1991.

*Escherichia coli* is often used as a host cell for the expression of large amounts of heterologous proteins by recombinant DNA techniques. The process of this invention is especially useful for the purification of water-soluble forms of PBP 2a expressed in *Escherichia coli* cells. Because *E. coli* itself has penicillin binding proteins, purification of PBP 2a$^s$ expressed in *E. coli* is especially important so as to avoid false-positives that may occur when carrying out the above-mentioned purification procedure.

As this invention provides a process for purifying PBP 2a$^s$, it is necessary that the PBP 2a protein be present in water-soluble form within the host cell. As described in Example 1, certain growth conditions are necessary in order to ensure that the host cell expresses PBP 2a$^s$.

In carrying out the process of this invention a crude cell extract solution is obtained from wet whole cells that contain PBP 2a$^s$ by harvesting these cells from culture medium in a conventional manner, such as centrifugation. Host cells containing PBP 2a$^s$ may be stored at −70° C. until needed. The cells are lysed by various methods to produce the crude cell extract. For example, about 200 g of thawed cells are resuspended in a buffer such as sodium phosphate buffer, pH 8.0 (SP8). The cells are then rendered more susceptible to sonic disruption and the released DNA is digested by addition of lysozyme, DNase, and 10 mM MgSO$_4$ with incubation at about 4° C. Cells are then lysed using methods such as sonication. The cellular lysate is then fractionated to obtain a proteinaceous solution substantially free from cellular debris. The preferred method of fractionation is by centrifugation, followed by filtration of the supernatant through glass wool. The resulting filtrate is the crude cell extract (alternatively, "crude extract").

According to the process of the present invention, the crude cell extract is then contacted at about pH 8 with an anionic-exchange resin such as Q-Sepharose (QS, Pharmacia, Inc., Piscataway N.J.), DEAE Sepharose, or Mono Q. The preferred method of contacting the crude cell extract and anionic-exchange resin is by chromatography. Two forms of PBP 2a$^s$ ("bound PBP 2a$^s$" and "unbound PBP 2a$^s$") are separated by this procedure. The unbound form does not bind to the anionic-exchange resin. The predominant form of PBP 2a$^s$ resulting from this step of the purification process is unbound PBP 2a$^s$. The PBP 2a$^s$ bound to the anionic-exchange resin is eluted with a linear salt gradient (e.g., monovalent salts such as KCl or NaCl) at about pH 8.

The unbound PBP 2a$^s$-containing fractions are then contacted at about pH 6.0 with a cationic-exchange resin such as, CM-Sepharose (CM, Pharmacia, Inc.), CM-Trisacryl, or S-Sepharose. The bound PBP 2a$^s$-containing fractions are contacted with the cationic-exchange resin using an identical procedure. Both bound PBP 2a$^s$ and unbound PBP 2a$^s$ bind to the cationic-exchange resin. Chromatography is the preferred method of contacting the bound PBP 2a$^s$ and unbound PBP 2a$^s$ with the cationic-exchange resin. Both bound PBP 2a$^s$ and unbound PBP 2a$^s$ are eluted from the cationic-exchange resin with a linear salt gradient (e.g., monovalent salts such as KCl or NaCl).

Following concentration and dilution to reduce salt concentration, bound PBP 2a$^s$ and unbound PBP 2a$^s$-containing fractions are contacted at about pH 8.0 over a dye-ligand resins capable of binding PBP 2a$^s$. Dyes that are cross-linked to agarose are the preferred dye-ligand resins. Such dye-ligand resins include Reactive Blue 4 (resin:cross-linked agarose; dye: Pricion Reactive Blue 4; Sigma Chemical Co., St. Louis Mo., Catalog No. R8754), Reactive Green 5 (resin:cross-linked agarose; dye: Pricion Reactive Green 5; Sigma Catalog No. R8630), Reactive Green 19 (resin:cross-linked agarose; dye: Pricion Reactive Green 19; Sigma Catalog No. R4004), Reactive Red 120 (resin:cross-linked agarose; dye: Pricion Reactive Red 120; Sigma Catalog No. R9129), Reactive Brown 10 (resin:cross-linked agarose; dye: Pricion Reactive Brown 10; Sigma Catalog No. R8629), Reactive Blue 72 (resin:cross-linked agarose; dye: Pricion Reactive Blue 72; Sigma Catalog No. R8505), Matrex™ Blue A (resin:cross-linked agarose; dye: Cibacron 3GA; Amicon, Beverly, Mass., Catalog No. 19011), Martex™ Blue B (resin:cross-linked agarose; dye: Pricion Turquoise H-7G130; Amicon, Catalog No. 19411), Martex™ Red A (resin:cross-linked agarose; dye: Pricion Red HE3B; Amicon, Catalog No. 19111),and Matrex™ Green A (resin::cross-linked agarose; dye: Pricion Olive P-7G; Amicon, Catalog No. 19311).

Many dye-ligand resins will be useful in the process of this invention. It will be recognized that a particular dye-ligand resin may be tested for the ability to bind PBP 2a$^s$ by substituting in the process of this invention the dye-ligand resin to be tested for one of the dye-ligand resins listed above. The eluate from the dye-ligand resin is then tested for the presence of PBP 2a$^s$ as described above. In this manner, it was determined that dye-ligand resins Matrex™ Orange A (resin:cross-linked agarose; dye: Pricion Yellow HA; Amicon, Catalog No. 19211), Reactive Yellow 3 (resin:cross-linked agarose; dye: Pricion Yellow 3; Sigma Catalog No. R3757), and Reactive Yellow 86 (resin:cross-linked agarose; dye: Pricion Yellow 86; Sigma Catalog No. R8504) do not bind PBP 2a$^s$.

The preferred method of contacting bound PBP 2a$^s$ and unbound PBP 2a$^s$ with the dye-ligand resin is by chromatography. The PBP 2a$^s$ from the bound and unbound pools are allowed to react with the dye-ligand resin prior to washing. Elution from the dye-ligand resin is accomplished with a slow, linear salt gradient (e.g., monovalent salts such as KCl or NaCl) at about pH 8.0.

Occasionally a low molecular weight contaminant is found in either the bound PBP 2a$^s$ or unbound PBP 2a$^s$-containing fractions of the dye-ligand resin eluate. Following concentration, the contaminant is effectively removed by using molecular sizing chromatography. Numerous commercial resins and columns are available for this purpose. Such resins include, but are not limited to N.J., HiLoad Sephacryl S-200 HR (Pharmacia, Inc., Piscataway, N.J.), HiLoad Superdex 200 (Pharmacia), Sephadex G-200 (Pharmacia) or Ultrogel AcA 44 (Sepracor, Marlborough Mass.). Preferably, HiLoad Sephacryl S-200 HR is equilibrated and eluted with sodium phosphate buffer at about pH 8.

The following examples are intended to assist in the further understanding of the invention. Particular materials employed, species, and conditions are intended to be further illustrative of the invention and not limiting the reasonable scope thereof. Procedures for the manipulation and analysis of DNA were performed essentially as described by Sambrook et al., 1989, *Molecular Cloning: a Laboratory Manual*, Cold Spring Harbor Laboratory Press, Cold Spring Harbor, N.Y. Conditions for restriction enzyme reactions were those recommended by the manufacturers (Boehringer Mannheim (BM), Indianapolis, Ind.; New England Biolabs (NEB), Beverly, Mass.; Bethesda Research Labs (BRL), Gaithersburg, Md.).

EXAMPLE 1

Production of Soluble PBP 2a$^s$

A. Culture Conditions

*Escherichia coli* RV308 was transformed with the expression plasmid pEWSA54. *Escherichia coli* RV308/pEWSA54 was deposited in the permanent culture collection of the Northern Regional Research Laboratory (NRRL), United States Department of Agriculture Service, Peoria, Ill. 61604, on May 6, 1993, and is available under accession number B-21089. Plasmid pEWSA54 contains DNA encoding a runaway replicon, and a Bacillus vegetative promoter positioned to drive the expression of the modified *Staphylococcus aureus* 27r mecA gene which lacks the putative transmembrane domain. A runaway replicon is a temperature sensitive plasmid copy control mechanism. At elevated temperatures (e.g., over 35° C.) copy control is lost and the cell will generate high numbers of plasmids. While plasmid pEWSA54 has a runaway replicon, the conditions used for growth (28° C.) and constitutive production of PBP 2a$^s$ from plasmid pEWSA54 in an *Escherichia coli* host cell as described herein do not allow for loss of copy control. As shown in Table 1, PBP 2a$^s$ was produced when the *Escherichia coli* host cell was cultured below about 28° C. However, when the host cells were cultured at about 35° C., the pEWSA54 product was a nonmembrane bound, water-insoluble granule that was not amenable to the purification process of this invention. Thus, shake flasks cultures of *Escherichia coli* RV308/pEWSA54 were grown under kanamycin selection (50 µg/ml) in TY broth containing 8 grams (g) of tryptone, 5 g of NaCl and 5 g of yeast extract per liter. A maximal gene expression at 1–2% of total soluble protein was attained at 28° C. in 24 hours as shown in Table 1.

TABLE 1

Temperature Optimization for Production of PBP 2a$^s$ by *Escherichia coli* RV308/pEWSA54

| Protein Form | Temperature (°C.) | | |
|---|---|---|---|
| | 23 | 28 | 35 |
| Granular | − | − | +++ |
| Soluble | ++ | ++++ | − |

A seed lot was prepared by growing *Escherichia coli* RV308/pEWSA54 at 30° C. in L broth (10 g/L tryptone, 5 g/L yeast extract, and 5 g/L NaCl) plus 1% glucose under kanamycin selection. One ml aliquots were preserved in the vapor phase of liquid nitrogen. Inoculum for a 10 L fermentation was produced in an overnight culture of *E. coli* RV308/pEWSA54 grown in L broth plus glucose and kanamycin (1 vial of seed lot per 100 ml of culture) at 30° C. Fifty ml of the overnight culture was used to inoculate 10 L of fermentation broth (40 g tryptone, 20 g yeast extract, 10 g NaCl and 2% glucose per liter). The culture was controlled at 27° C., pH 7.0, and a dissolved $O_2$ concentration greater than 30%. A 10% NZ-Amine L feed (Sheffield Products, Norwich, N.Y.) was started when the glucose had been depleted. The culture was harvested at about 24 hours. The presence of glucose severely limited the expression of PBP $2a^s$ in both shake flask and fermenter cultures. A small amount of glucose was tolerable in the fermenter cultures since a reasonable cell mass could not be attained without it. However, if glucose was fed to maintain cell metabolism after the initial source was depleted, PBP $2a^s$ production was severely limited.

B. Generation of Crude Cell Extract

Cells containing PBP $2a^s$ from the 10 L fermentation were harvested by centrifugation and stored at −70° C. until needed. Approximately 200 g of cells were resuspended in 200 ml of 50 mM sodium phosphate buffer, pH 8.0 (SP8). After thawing, lysozyme (1 mg/gm cells), DNase (1 µg/ml) and 10 mM $MgSO_4$ were added and the suspension was stirred at 4° C. for 1 hour to render the cells more susceptible to sonic disruption and to digest released DNA. Cells were broken by five 1 minute sonic bursts. Sonication debris was removed by centrifugation (48,000×g) for 20 minutes followed by filtration of the supernatant through glass wool. The resulting filtrate was the crude cell extract and typically contained 1–2% PBP $2a^s$.

EXAMPLE 2

Purification of PBP $2a^s$ From Crude Cell Extracts

Purification of PBP $2a^s$ was carried out at 4° C. Crude extract was loaded onto a Q-Sepharose (QS) column (5.0× 11.0 cm, Pharmacia, Inc. Piscataway, N.J.) previously equilibrated with sodium phosphate buffer, pH 8.0 (SP8). The column was washed with 3 column volumes of SP8 and proteins were eluted with a linear gradient of 0–0.5M KCl in five column volumes of SP8. Protein, SDS-PAGE and $I^{125}$-penicillin V binding assay revealed that the predominant form of PBP $2a^s$ from the crude cell extract was not bound to the QS column. Protein concentrations were determined by the method of Bradford, 1976, *Anal. Biochem.* 72:248–254, using bovine serum albumin as the standard. Assays employing $I^{125}$-penicillin V binding were done as previously described by Preston et al., 1990, *Antimicrobiol. Agents Chemother.* 34:718–721. $I^{125}$-penicillin V was synthesized as described by Blaszczak et al, 1989, *J. Labeled Compd. Radiopharmacol.* 27:401–406. The two protein forms (bound PBP $2a^s$ and unbound PBP $2a^s$) were further purified in parallel two-step procedures.

A combined pool of fractions from the Q-Sepharose chromatography step containing unbound PBP $2a^s$ was adjusted to pH 6.0 and loaded onto a CM-Sepharose column (2.5×20 cm, Pharmacia, Inc.), previously equilibrated with sodium phosphate buffer, pH 6.0 (SP6). The loaded column was washed with 3 column volumes of SP6 and proteins were eluted with a linear gradient of 0–1.5M KCl in 3 column volumes of SP6. Similarly, after concentration using a Centriprep-10 concentrator (Amicon Inc., Beverly, Mass.) followed by dilution with SP6 to reduce the KCl to less than 10 mM, the bound PBP 2as-containing fractions from the Q-Sepharose step were chromatographed using an identical CM-Sepharose procedure. Protein, SDS-PAGE and the $I^{125}$ penicillin V binding assay revealed that bound PBP $2a^s$ and unbound PBP $2a^s$ were effectively retained and further purified by the cation-exchange chromatography.

Both bound PBP $2a^s$ and unbound PBP $2a^s$-containing fractions from the CM-Sepharose step were concentrated and diluted with SP8 to reduce the KCl to less than 10 mM. Each dialyzed pool was loaded onto a Reactive Blue-4 Agarose column (5×15 cm for unbound protein and 2.5×18 cm for the bound protein, Sigma Chemical Co., St. Louis Mo.) previously equilibrated with SP8. The loaded proteins were allowed to react with the dye-ligand for 1 hour prior to washing with 3 column volumes of SP8. Elution of PBP $2a^s$ was accomplished with 3 column volumes of a slow, linear gradient of 0–1M KCl in SP8. Protein, SDS-PAGE and the binding assay showed that after the dye-ligand chromatography PBP $2a^s$ from peak fractions was >99% pure, based on laser densitometry. Typically, in excess of about 50 mg of unbound PBP $2a^s$ was recovered from 200 g of cells.

Occasionally a low molecular weight contaminant was found in either the unbound PBP $2a^s$ or bound PBP $2a^s$-containing fractions of the Reactive Blue-4 Agarose eluate. After concentration of the eluate, the contaminant was effectively removed by gel filtration on a HiLoad Sephacryl S-200 HR column (1.6×120 cm, Pharmacia) equilibrated and eluted with SP8. Based on laser densitometry, peak fractions contained greater than 99% PBP $2a^s$.

Electrospray Mass Spectroscopic analysis of both PBP $2a^s$ pools confirmed their purity and revealed that they had identical molecular mass of about 74,000. The observed mass was consistent with the calculated mass based on the amino acid sequence. The amino acid compositions of the two proteins were also identical. The amino terminal sequences of the purified proteins were identical to the sequence for the truncated PBP 2a derived from the DNA sequence of the expressed gene. These results provided conclusive evidence that the purified, $I^{125}$-penicillin V binding protein was PBP $2a^s$. The isoelectric point (pI) of the bound PBP $2a^s$ has been estimated to be between pH 4 and 5 by Capillary Zone Electrophoresis.

We claim:

1. A process for isolating in substantially purified form water soluble penicillin binding protein 2a from a biological cell comprising:

a) lysing said cell;

b) fractionating the cell lysate to obtain a proteinaceous solution substantially free from cellular debris;

c) contacting, at a pH of about 8, the proteinaceous solution obtained in b) with an anion-exchange resin that is not capable of binding the water soluble penicillin binding protein 2a contained in the proteinaceous solution;

d) collecting water soluble penicillin binding protein 2a-containing fractions of the solution that do not bind to the anion-exchange resin;

e) contacting, at a pH of about 6, the water soluble penicillin binding protein 2a-containing fractions of d) with a cation-exchange resin capable of binding the water soluble penicillin binding protein 2a;

f) eluting the water soluble penicillin binding protein 2a from the cation-exchange resin with a linear salt gradient;

g) concentrating and diluting the eluate of step f) to reduce salt concentration;

h) contacting, at a pH of about 8, the eluate obtained in g) with a dye-ligand resin selected from the group consisting of Reactive Blue 4, Reactive Green 5, Reactive Green 19, Reactive Red 120, Reactive Brown 10, Reactive Blue 72, Matrex™ Blue A, Matrex™ Blue B, Matrex™ Red A, and Matrex™ Green A; and i) eluting the water soluble penicillin binding protein 2a from the dye-ligand resin with a linear salt gradient.

2. A process of claim 1 wherein the PBP $2a^s$ is PBP $2a^s$ 27r.

3. A process of claim 1 wherein the biological cell is *Escherichia coli*.

4. A process of claim 1 wherein the water soluble penicillin binding protein 2a obtained in step i) is separated from coeluting contaminants by molecular sizing chromatography.

5. A process of claim 2 wherein the biological cell is *Escherichia coli*.

6. A process of claim 5 wherein the water soluble penicillin binding protein 2a obtained in step i) is separated from coeluting contaminants by molecular sizing chromatography.

* * * * *